United States Patent
Peyman (10) Patent No.: US 7,186,266 B2
(45) Date of Patent: Mar. 6, 2007

(54) BIFOCAL INTRAOCULAR TELESCOPE FOR LOW VISION CORRECTION

(75) Inventor: Gholman A. Peyman, New Orleans, LA (US)

(73) Assignee: Teledioptic Lens System, LLC, Pittsboro, NC (US)

(*) Notice: Subject to any disclaimer, the term of this patent is extended or adjusted under 35 U.S.C. 154(b) by 89 days.

(21) Appl. No.: 11/038,320

(22) Filed: Jan. 17, 2005

(65) Prior Publication Data
US 2006/0100702 A1 May 11, 2006

Related U.S. Application Data

(63) Continuation-in-part of application No. 10/873,495, filed on Jun. 23, 2004, now abandoned, and a continuation-in-part of application No. 10/600,371, filed on Jun. 23, 2003, and a continuation-in-part of application No. 10/455,788, filed on Jun. 6, 2003.

(51) Int. Cl.
*A61F 2/16* (2006.01)

(52) U.S. Cl. .................................... 623/6.34

(58) Field of Classification Search ....... 623/6.32–6.36
See application file for complete search history.

(56) References Cited

U.S. PATENT DOCUMENTS

| | | | | |
|---|---|---|---|---|
| 5,391,202 A | * | 2/1995 | Lipshitz et al. | 623/6.34 |
| 5,928,283 A | * | 7/1999 | Gross et al. | 623/6.34 |
| 6,596,026 B1 | * | 7/2003 | Gross et al. | 623/6.34 |
| 2004/0117013 A1 | * | 6/2004 | Schachar | 623/6.36 |

FOREIGN PATENT DOCUMENTS

FR 2666735 A * 3/1992

* cited by examiner

*Primary Examiner*—Thomas Barrett
*Assistant Examiner*—David A. Izquierdo
(74) *Attorney, Agent, or Firm*—Bell, Boyd & Lloyd LLC; Jeffrey J. Howell (57) ABSTRACT

An intraocular lens system for correcting vision in the eye, including a first lens adapted to be inserted into the eye substantially along the main optical axis and a second lens adapted to be inserted into the eye substantially along the main optical axis, spaced from and in series with the first lens, such that the first and second lenses form a teledioptic lens system.

39 Claims, 6 Drawing Sheets

BIFOCAL INTRAOCULAR TELESCOPE FOR LOW VISION CORRECTION

CROSS REFERENCE TO RELATED APPLICATIONS

This application is a continuation-in-part of U.S. application Ser. No. 10/455,788, filed Jun. 6, 2003, entitled "TELEDIOPTIC LENS SYSTEM AND METHOD FOR USING THE SAME," U.S. application Ser. No. 10/600,371, filed Jun. 23, 2003, entitled "TELEDIOPTIC LENS SYSTEM AND METHOD FOR USING THE SAME", and U.S. application Ser. No. 10/873,495, filed Jun. 23, 2004, and entitled "BIFOCAL INTRAOCULAR TELESCOPE FOR LOW VISION CORRECTION". The entire contents of each of these applications are incorporated herein by reference.

FIELD OF THE INVENTION

The present invention generally relates to an intraocular lens for implantation in an eye. More specifically, the present invention relates to an intraocular telescope for correction of low vision caused by macular degeneration.

BACKGROUND OF THE INVENTION

Macular degeneration has become one of the leading causes of blindness in adults. This disease affects the central retinal area known as the macula. The macula is responsible for acute vision—i.e., vision for such things as driving or reading a newspaper. Macular degeneration can lead to a gradual or sudden loss of vision to the level of 20/200 or less. Commonly, loss of vision only affects the central macular area of about 0.25 to 4 square millimeters, and does not usually progress beyond this area, thereby leaving 95–99% of the retina unaffected. Thus, reading and driving vision can be lost, while peripheral vision remains intact. This condition is often referred to as low vision.

Most cases of macular degeneration are untreatable, although laser photocoagulation has been successful in certain instances. Telescopic systems that attach to eye glasses also have been used for many years to improve vision in patients with macular degeneration. These systems, which work by increasing the retinal image of a given object, have not been very successful because they restrict the visual field to about 11° so that normal activity is not possible. They are also large and bulky. Attempts have been made to increase the visual field by putting part of the telescope within the eye. A Galilean telescope is useful for this purpose and consists of a converging objective lens and a diverging ocular lens, which together produce a telescopic effect.

U.S. Pat. Nos. 4,666,446 and 4,581,031, both to Koziol and Peyman, and both of which are incorporated by reference herein, each disclose intraocular lenses which are implanted in the eye in place of the natural lens to redirect the rays of light to minimize the adverse affect on vision caused by the macular degeneration of the eye. For example, U.S. Pat. No. 4,666,446 discloses an intraocular lens comprising a first portion including a diverging lens and a second portion including a converging lens. The converging lens provides the eye with substantially the same focusing ability of the natural lens prior to implantation of the intraocular lens. Thus, the eye will have decreased visual acuity due to the macular degeneration, but will also have unrestricted peripheral vision. The diverging lens, on the other hand, when combined with a converging lens positioned outside of the eye (e.g., a spectacle lens), provides a magnified image with increased visual acuity but a restricted visual field. Therefore, this type of intraocular lens creates a teledioptic lens system, which provides the patient with the choice of unmagnified but peripherally unrestricted vision or magnified but peripherally restricted vision.

U.S. Pat. No. 6,197,057 to Peyman and Koziol, the entire contents of which are herein incorporated by reference, relates to a lens system that combines a high plus lens with a plus and minus intraocular lens (IOL), so that the lens system works in a manner similar to a Galilean telescope. Generally the high plus lens is outside the eye (i.e., in glasses or spectacles or in a contact lens) and the plus and minus lens is an IOL that replaces or works in conjunction with the natural lens of the patient (See FIGS. 1 and 2).

U.S. Pat. Nos. 4,074,368 and 6,596,026 B1, the entire contents of which are herein incorporated by reference, both disclose telescopic implants for implantation within an eye. These implants are designed to replace the natural lens in the eye with a telescope. They are rigid devices requiring a large incision in the eye to implant.

Although all of these systems are beneficial to patients with macular degeneration, a continuing need exists for an intraocular implant that can correct for low vision in the eye.

SUMMARY OF THE INVENTION

An object of the present invention is to provide a telescopic intraocular lens for implantation in an eye to correct for macular degeneration.

Another object of the present invention is to provide an intraocular lens for implantation in an eye that provides both unmagnified and peripherally unrestricted vision and magnified and peripherally restricted vision to correct for macular degeneration.

A further object of the present invention is to provide an intraocular lens for implantation in an eye to create a lens system that redirects rays of light away from a diseased portion of the retina in the eye and focuses those rays onto an un-diseased area of the eye.

Yet another object of the present invention is to provide an intraocular lens implant that is small enough to be implantable through a relatively small incision in the eye, and can provide bifocal correction to the eye.

These and other objects of the invention are achieved by an intraocular lens system for correcting vision in the eye, including a first lens adapted to be inserted into the eye substantially along the main optical axis and a second lens adapted to be inserted into the eye substantially along the main optical axis, spaced from and in series with the first lens, such that the first and second lenses form a teledioptic lens system.

Other objects, advantages, and salient features of the present invention will become apparent from the following detailed description, which, taken in conjunction with the annexed drawings, discloses preferred embodiments of the invention.

BRIEF DESCRIPTION OF THE DRAWINGS

Referring to the drawings which form a part of this disclosure.

DETAILED DESCRIPTION OF THE INVENTION

Referring to FIGS. 1–4, an eye 10 includes a cornea 12, iris 14, natural lens 16, zonular ligaments 18, ciliary sulcus 20, retina 22, and macula 24. The natural lens 16, zonular ligaments 18, and ciliary sulcus 20 divide the eye into an anterior chamber 26 and a posterior chamber 28. The macula 24 is located at the center of the retina 22, and is responsible for providing acute vision, such as that necessary for driving or reading. An intraocular telescopic lens implant 30 in accordance with the invention is implanted in the anterior chamber 26 of the eye 10. The intraocular telescopic lens implant 30 has a telescope portion 32 surrounded by a substantially transparent peripheral portion 34.

Figure 1:
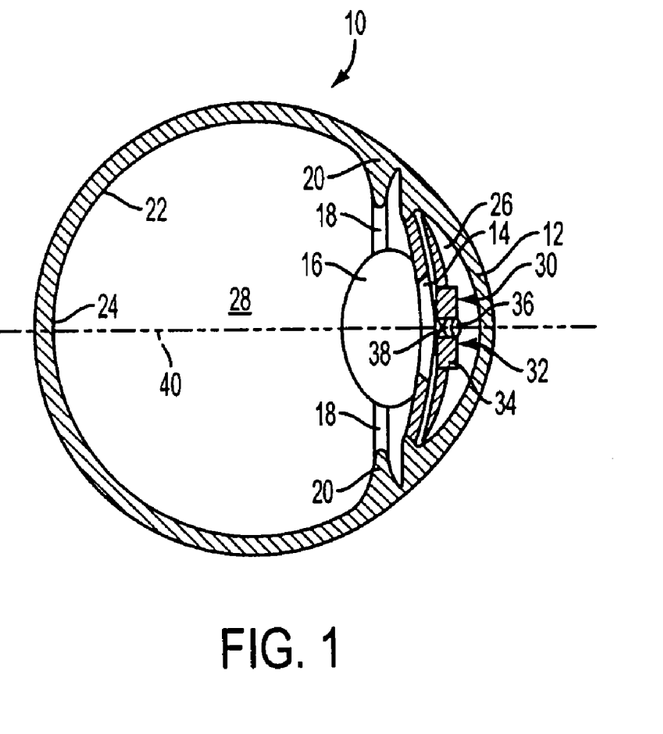
FIG. 1 is a cross-sectional view in side elevation of a human eye with an intraocular implant according to a first embodiment of the present invention.
Figure 2:
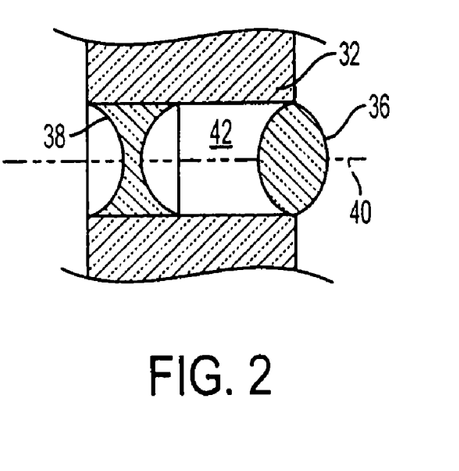
FIG. 2 is an enlarged cross-sectional view in side elevation of the telescope portion of the implant shown in FIG. 1 having a plus and a minus lens therein.

The telescope portion 32 allows light to pass therethrough and has a bi-convex converging, or plus, lens 36 and a bi-concave diverging, or minus, lens 38. The lenses 36, 38 are aligned along an optical axis 40 to form a Galilean telescope. Preferably, the lenses are about 1–2 mm in diameter. The diverging lens 38 has a refractive index between −30 and −90 diopters, as measured in water. The converging lens 36 has a refractive index between +30 and +80 diopters, as measured in water. The lenses 36, 38 are rigidly received in and fastened as necessary to the wall of a substantially cylindrical aperture 39 formed in the peripheral portion 34 of the implant 30, forming a cavity 42 therebetween. The cavity 42 is preferably vacuum sealed. The use of a vacuum in cavity 42 increases the refractive index, allowing for a smaller telescope. The lenses 36, 38 can be forced-fit or adhered to the aperture 39 so they do not move relative thereto. The lenses 36, 38 are spaced approximately 0.5 to 5 mm apart, depending on their particular optical properties, so that the telescope portion is approximately 0.3 to 5 mm thick.

Figure 3:
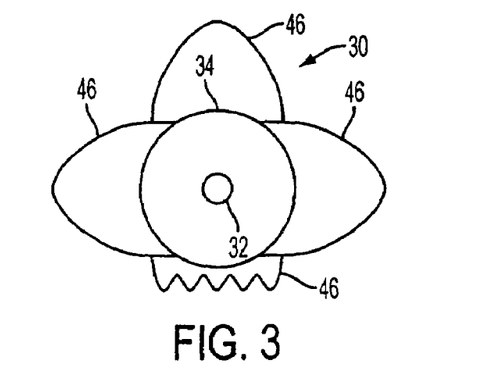
FIG. 3 is a top plan view of the intraocular implant shown in FIG. 1 prior to implantation.
Figure 4:
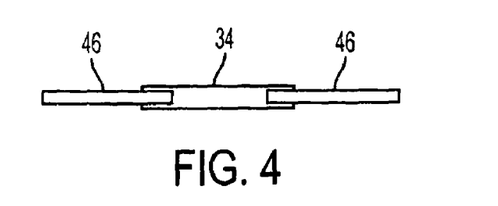
FIG. 4 is a side elevational view of the intraocular implant shown in FIG. 3.

FIGS. 3 and 4 illustrate the intraocular telescopic implant 30 prior to implantation. The substantially circular peripheral portion 34 surrounding or substantially surrounding the telescope portion 32 is made of a biocompatible, transparent, optical material. Peripheral portion 34 is preferably flexible, but can be rigid or partially rigid and partially flexible or any other suitable configuration. The peripheral portion has a diameter of approximately 2 to 6.5 mm, and a thickness of approximately 0.05 to 1 mm. The peripheral portion 34 may have refractive powers to correct for refractive errors in the eye, or may have substantially no refractive powers. The peripheral portion 34 may also have varying thickness and refractive power to correct for any astigmatism in the eye. Further, the peripheral portion 34 can have multiple focal adjustments—i.e., bifocal—to correct for and provide multiple refractive corrections. Arranged around the edge of the peripheral portion 34 are from two to four haptics 46 for fastening the implant in the anterior chamber of the eye. Four haptics are shown in the illustrated embodiment, but any number of haptics may be used. With the haptics, the diameter of the implant is approximately 10–14 mm.

Figure 10:
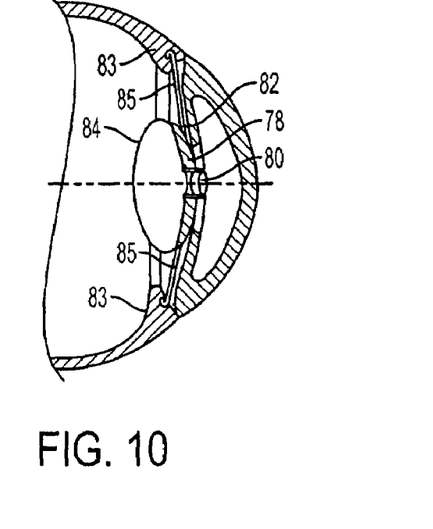
FIG. 10 is a cross-sectional view in side elevation of a human eye with an intraocular implant according to a fourth embodiment of the present invention.

To implant the intraocular telescopic implant in the eye, an incision is made in the eye through the use of a microkeratome, laser, or other suitable surgical device. The implant 30 is folded or rolled up, and inserted into the anterior portion of the eye through the incision. The implant 30 is allowed to unfold or unroll, and the haptics 46 extend into the anterior chamber angle (i.e. the angle formed where the iris and the cornea meet) and fixate the implant into the anterior chamber 26 of the eye 10. Since the implant 30 is foldable, the incision is relatively small. This is beneficial because any incision to the eye can cause astigmatisms in the eye and require varying healing periods. The implant 30 may also be implanted into the posterior chamber, as shown in FIG. 10 and discussed below, or implanted into the capsular bag.

In use, the light rays that enter the eye from the central field of vision are substantially parallel to the axis 40 of the telescopic implant 30. Because they are parallel to the axis of the telescope, the rays enter the telescope and are magnified and projected onto the retina to provide enhanced acute vision for the central field of vision. At the same time, light rays from the peripheral field are unobstructed by the transparent peripheral portion 34 of the lens implant so that the patient retains unrestricted peripheral vision. Furthermore, because the peripheral portion of the implant is transparent, a doctor examining a patient's retina has an unobstructed view of the retina.

The lenses 36, 38 illustrated in FIGS. 1–2 are conventional bi-convex and bi-concave lenses. The conventional lenses are refractive lenses—i.e. they utilize refraction to modify how light propagates through the lenses to change the focal point of the lenses. The lenses in the telescopic implant 30, however, may have any desirable shape or configuration.

Figure 5:
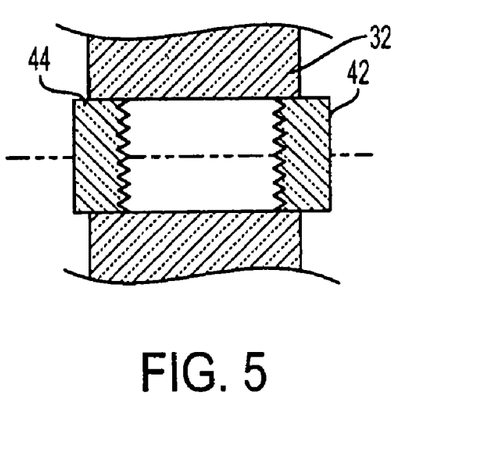
FIG. 5 is an enlarged cross-sectional view in side elevation of a modified telescope portion of the present invention using diffractive lenses.

FIG. 5 illustrates a telescope portion 32 which uses diffractive lenses 42, 44. Diffractive lenses, such as Fresnel lenses, utilize diffraction to modify how light propagates through the lenses to change the focal point of the lenses. Diffractive lenses are advantageous because they are very thin as compared to conventional refractive lenses. Other suitable lenses include those made by ThinOptx, Inc. of Abingdon, Va. ThinOptx, Inc. manufactures intraocular lenses that are approximately 100 microns thick with +/−25 diopters of correction. Further details regarding these lenses are found in U.S. Pat. Nos. 6,666,887 and 6,096,077, which are hereby incorporated by reference in their entirety. When using technology such as this, the telescope portion can be about 2–3 mm, preferably about 2 mm thick.

Figure 6:
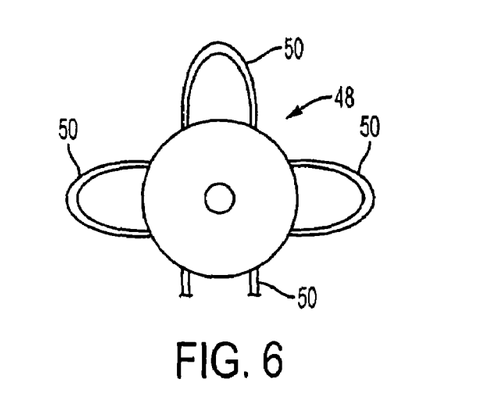
FIG. 6 is a top plan view of an intraocular implant similar to that shown in FIGS. 3 and 4, but using U-shaped haptics.
Figure 7:
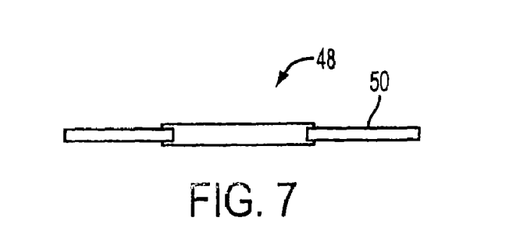
FIG. 7 is a side elevational view of the intraocular implant shown in FIG. 6.

The implant 30 illustrated in FIG. 1 uses haptics 46 which affix the implant into the anterior chamber angle. FIGS. 6 and 7 illustrate an implant 48 which uses alternative, substantially U-shaped haptics 50. Upon implantation, the U-shaped haptics 50 overlie the iris and can be clipped to the iris to provide added stability to the implant. One skilled in the art will recognize that although two preferred styles of haptics are specifically disclosed herein, there are a wide variety of known haptics and any suitable haptics, such as J-shaped haptics, can be used with the present invention.

Figure 8:
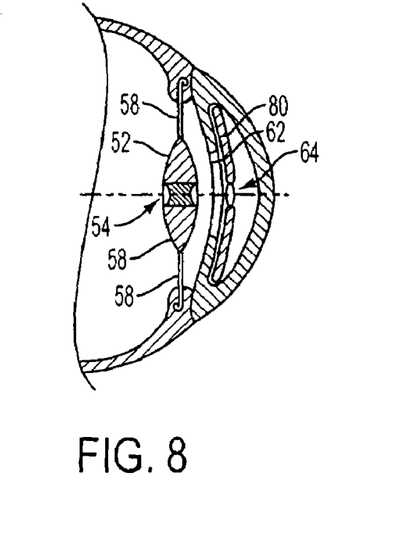
FIG. 8 is a cross-sectional view in side elevation of a human eye with an intraocular implant according to a second embodiment of the present invention with an artificial IOL substituted for the natural lens.

Embodiment of FIG. 8

FIG. 8 shows a second embodiment of the present invention. In this embodiment, the natural lens of the eye is replaced with an artificial lens 52. The artificial lens 52 has a central portion 54, a peripheral portion 56, and is fastened into the posterior chamber by haptics 58. The peripheral portion 56 of the lens 52 is a generally converging lens, much like the natural lens which it replaces. The central portion 54, however, is a diverging lens with a high negative refractive index. An anterior implant 60 is located in the anterior chamber of the eye. The anterior implant 60 has a transparent peripheral portion 62 and a central portion 64. The central portion 64 is a lens with a high positive refractive index. The anterior implant central portion 64 is aligned with the artificial lens central portion 54, forming a telescope for enhancing low vision. The peripheral portion 62 has the same characteristics as peripheral portion 34 described above regarding the first embodiment of FIGS. 1–4.

Figure 9:
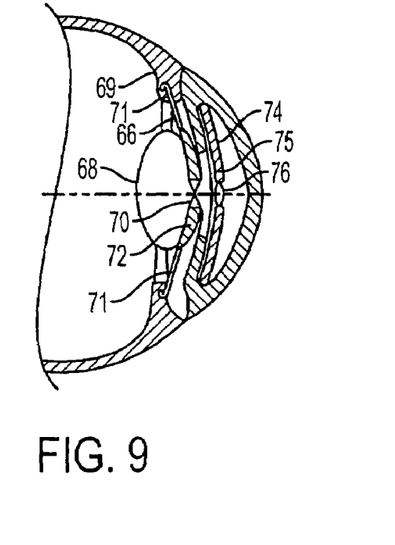
FIG. 9 is a cross-sectional view in side elevation of a human eye with an intraocular implant according to a third embodiment of the present invention used with the natural lens.

Embodiment of FIG. 9

FIG. 9 illustrates a third embodiment of present invention. In this embodiment, a first intraocular implant 66 is placed immediately adjacent the primary lens 68 and placed in the ciliary sulcus 69 of the posterior chamber by haptics 71. The illustrated primary lens 68 is a natural lens, but may also be an artificial intraocular lens. The central portion 70 of the implant 66 is a lens with a high negative refractive index and is surrounded by a peripheral portion 72, which has the same characteristics as portion 34 described above. A second intraocular implant 74 is placed in the anterior chamber of the eye. The second intraocular implant 74 has a central lens portion 76 with a positive refractive index and a peripheral portion 75 surrounding lens portion 76. Preferably, the central portions 70, 76 of the two implants 66, 74 are aligned along the main optical axis (however, these lenses can be aligned in any suitable manner), forming a telescope as discussed above regarding the embodiment of FIGS. 1–4.

Embodiment of FIG. 10

FIG. 10 shows a fourth embodiment of the present invention. In this embodiment, the intraocular implant 78 has a telescope portion 80 attached to a peripheral portion 82. The peripheral portion 82 is placed directly onto the primary lens 84 and is attached to the ciliary sulcus 83 by haptics 85. The illustrated primary lens is a natural lens, but may also be an artificial intraocular lens. The telescope portion 80 preferably is formed from a flexible material, similar to portion 34. Additionally, telescope portion can be configured as tube 80 (FIGS. 12–14) having similar characteristics as portion 34 or it can be formed as structure or telescope portion 129 having struts or extension members (FIG. 18).

Figure 18:
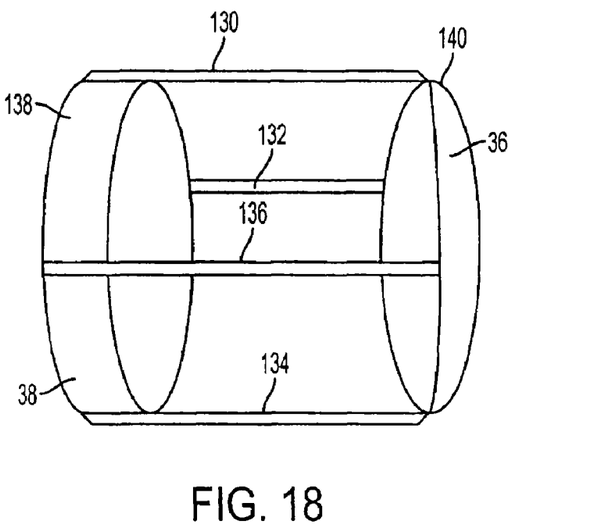
FIG. 18 is a perspective view of an alternative telescope portion for providing a teledioptic lens system.

As shown in FIG. 18, each strut 130, 132, 134, 136 is attached to the periphery 138 of lens 38 (in any conventional manner, such as adhesive or any other suitable means) and extends to the periphery 140 of lens 36 and attaches thereto in the same or substantially similar manner. The telescope portion 129 can have any suitable number of struts. For example, the telescope portion can have as few as one strut or as many as desirable. The struts are preferably formed from a material that can be flexible, such as the material disclosed above or portion 34 or any other suitable material. By forming the telescope portion 129 in this manner, natural fluid from the eye can flow between the lenses of the telescope portion. Additionally, the entire structure including the telescope portion 129 and peripheral portion 82 can be folded when inserted into the eye and unfolded after entry into the appropriate chamber. This flexibility allows the implant 78 to be inserted into a smaller incision in the surface of the eye, thus reducing possible damage to the eye.

When implanted, the telescope portion preferably extends through the iris; however, it is noted that the telescope portion does not necessarily need to extend through the iris and it can be situated in the eye in any suitable manner. The peripheral portion 82 has the same characteristics as portion 34 described above.

Figure 11:
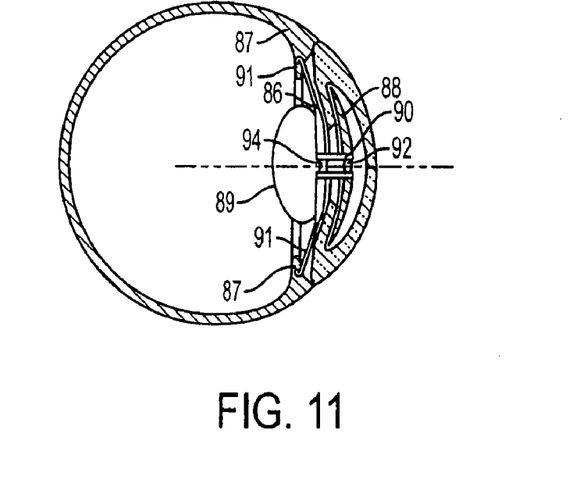
FIG. 11 is a cross-sectional view in side elevation of a human eye with an intraocular implant according to a fifth embodiment of the present invention.
Figure 12:
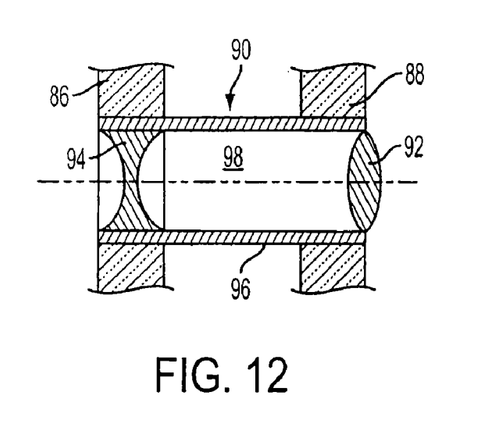
FIG. 12 is an enlarged cross-sectional view in side elevation of the telescope portion of the intraocular implant of FIG. 11 having a plus and a minus lens therein.
Figure 13:
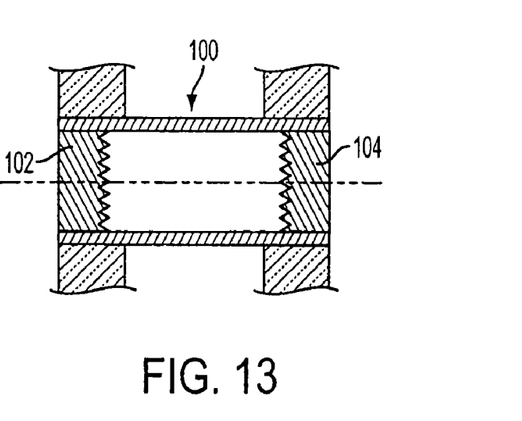
FIG. 13 is an enlarged cross-sectional view in side elevation of alternative telescope portion of the present invention for use with the embodiment of FIG. 11.
Figure 14:
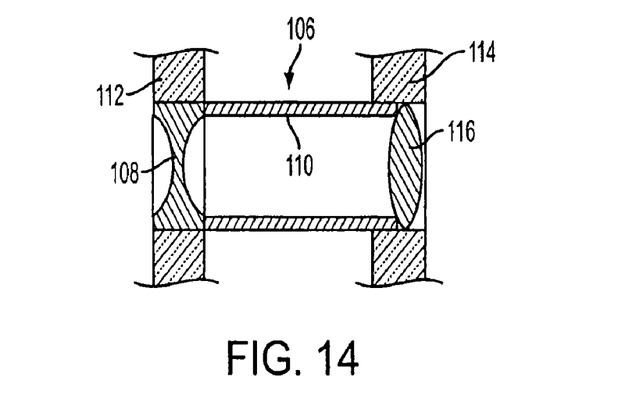
FIG. 14 is an enlarged cross-sectional view in side elevation of another alternative telescope portion for use with the embodiment of FIG. 11.

Although preferable, it is not necessary for the telescope portion 80 described in FIGS. 12–14 and telescope portion 129 described in FIG. 18 to be used with peripheral portions. For example, the telescope portion can be used with one peripheral portion, as disclosed in FIG. 10, two peripheral portions as disclosed in FIG. 11 or no peripheral portions. When used with no peripheral portions, the telescopic portion can be affixed inside the eye in any suitable manner, such as with haptics, adhesive or friction. Additionally, the telescopic portion can be affixed to the natural lens, an artificial lens or any other suitable structure (natural or artificial) inside the eye.

Embodiment of FIGS. 11 AND 12

FIGS. 11 and 12 show a fifth embodiment of the present invention. In this embodiment, a first peripheral portion 86 is located in the posterior chamber of the eye, immediately adjacent the primary lens 89. A second peripheral portion 88 is located in the anterior chamber of the eye. A telescope portion 90 is formed by a converging lens 92, a diverging lens 94, and a tubular canister 96. The tubular canister 96 is rigidly received in circular apertures in the two peripheral portions 86, 88 and connects the two peripheral portions 86, 88 through the iris. Preferably, the tubular canister and lenses 93 and 94 are flexible; however each can be rigid or any other suitable configuration.

The connection of the canister 96 at both the posterior and anterior chambers of the eye improves the stability of the telescope. The cavity 98 within tubular canister 96 may be vacuum sealed, or may contain air or water. To implant the telescope portion 90 of FIG. 12, the first peripheral portion 86 is inserted into the eye and placed in the sulcus 87 over the primary lens 89 by haptics 91. The illustrated primary lens 89 is a natural lens, but may also be an intraocular lens. The telescope portion 90 is then fastened to the first peripheral portion 86. The second peripheral portion 88 is inserted into the anterior chamber and is fastened to the telescope portion 90. The peripheral portions 86, 88 have the same characteristics as portion 34 described above. Furthermore, as described above, the telescope portion can be used with one peripheral portion, as disclosed in FIG. 10, two peripheral portions as disclosed in FIG. 11 or no peripheral portions.

FIGS. 13 and 14 show two additional telescope portions which are suitable for use in the embodiment of FIG. 11. The telescope portion 100 shown in FIG. 13 is similar to the one in FIG. 12, but uses diffractive or Fresnel lenses 102, 104 lenses instead of conventional refractive convex and concave lenses. In the telescope portion 106 shown in FIG. 14, the diverging lens 108 and canister 110 are fastened to the first peripheral portion 112 prior to implantation, and the connected pieces are implanted simultaneously. The second peripheral portion 114 and anterior lens 116 are then implanted, forming the telescope portion in situ. By assembling the telescope portion in this manner, the incision is kept to the smallest possible size.

The implantation of the lenses described herein does not necessarily need to occur during one operating procedure and can occur over a predetermined period of time (e.g., seconds, minutes, days, weeks, months or years)

Additionally, the configuration shown in FIG. 18 is suitable for this embodiment. For example, the telescope portion 129 can replace telescope portion 82. As described above, telescope portion 129 can have flexible struts that allow fluid to flow therebetween. Preferably, as described above, the struts are flexible, so that the entire lens system, including the telescope portion can be inserted into the smallest possible incision; however, the struts that be any suitable configuration (including rigid, if desired) and can the telescope portion can have any number of struts desired. Any above description of telescope portion 129 is application to this embodiment.

Furthermore, the telescope portions described herein can be used with an existing IOL. For example, an existing IOLs that has high minus portions can be supplemented with an IOL (e.g., a high plus lens) that is implanted into the posterior or anterior chamber of the eye (or any other suitable portion of the eye) forming a telescopic portion, as described herein. Additionally, the supplemental IOL can be connected to the existing lens using a strut(s) or a canister as described herein. The lenses described herein are merely exemplary, and the existing and supplemental lenses can be any shape or configuration, as long as a portion of each can be combined to form a teledioptic or telescopic lens system. Examples of suitable existing IOLs are described in U.S. Pat. No. 4,666,446 to Koziol (discussed above), the entire contents of which are incorporated herein by reference.

Embodiment of FIGS. 15–17, 19 and 20

Figure 15:
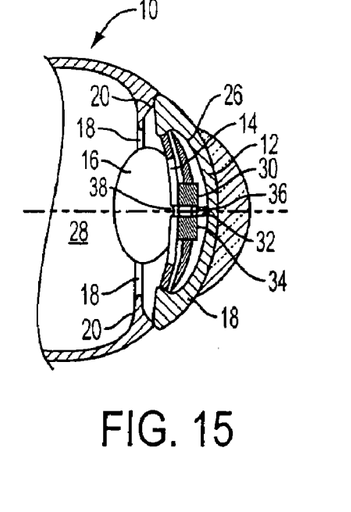
FIG. 15 is a cross-sectional view in side elevation of the embodiment of FIG. 1 further including a contact lens on the cornea.
Figure 16:
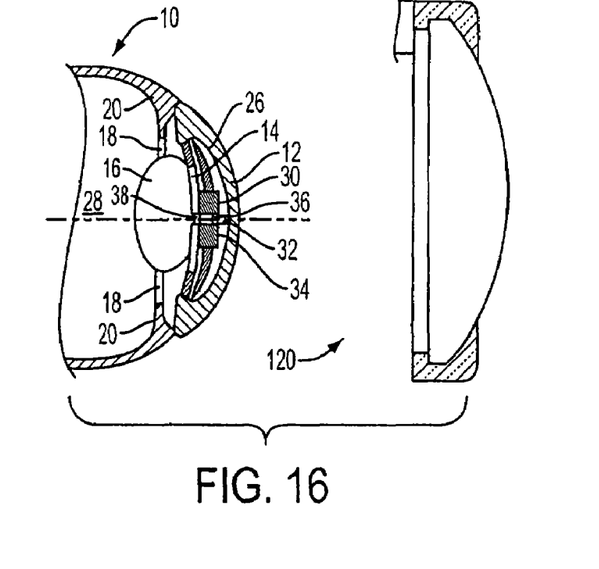
FIG. 16 is a cross-sectional view in side elevation of the embodiment of FIG. 1 further including an external spectacle.
Figure 17:
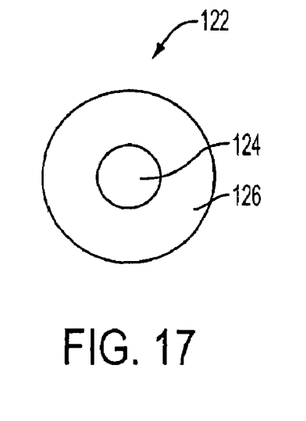
FIG. 17 is a top plan view of a bifocal contact lens.

Although the invention so far has been described without the use of a supplemental lens outside the eye, it should be understood that the implants can also be used in conjunction with a supplemental lens located outside the eye. FIGS. 15 and 16 illustrate this. In FIG. 15, a supplemental plus contact lens 118 is placed on the cornea 12. In FIG. 16, a supplemental spectacle with two plus lenses 120 is placed in the visual path. In both cases, the lenses 118, 120 have a positive refractive index. The use of supplemental lenses outside the eye allows for smaller implants inside the eye. Further, the use of supplemental lenses allows the construction and operation of the implants to be tailored to particular patients' desires. For instance, many individuals have a preferable reading distance (typically between 20 and 50 cm away from the eye) and a supplemental lens allows the focal distance to be tailored to coincide with an individual's preferred reading distance. The supplemental lenses themselves can be bifocal. FIG. 17 illustrates a contact lens 122. The central 2–7 mm portion 124 of the contact lens 122 provides refractive correction for near vision.

Preferably, the peripheral portion 126 (of either the contact lens or the spectacles) provides refractive correction for far vision. The peripheral portion 126 can have any refractive properties desired. For example, the peripheral portion can be used to correct myopia, hyperopia, astigmatism, presybyopia, or any other vision error, or the peripheral portion of the lens can have no refractive properties, thus allowing a patient with acceptable peripheral vision to see with no correction (other than the telescopic central correction).

Figure 19:
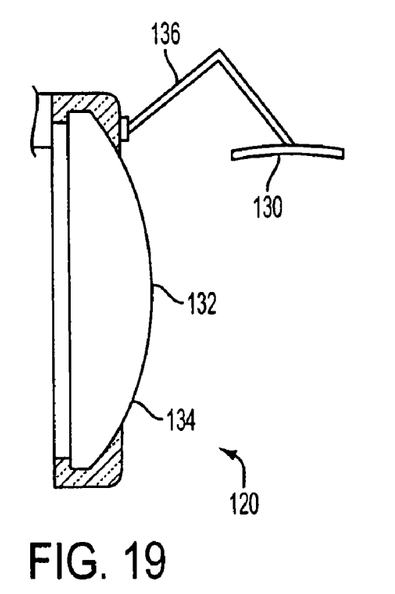
FIG. 19 is an elevational side view in section of an external spectacle with an opaque portion or member blocking light from passing through the central portion of the spectacle.
Figure 20:
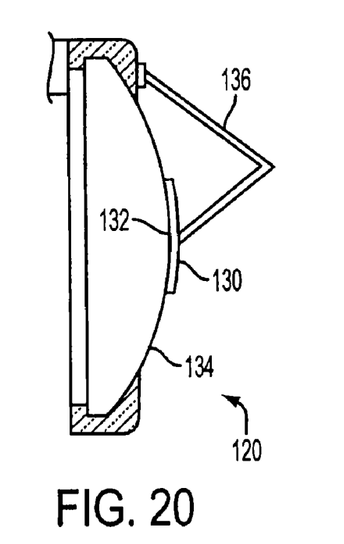
FIG. 20 is an elevational side view in section of the spectacles of FIG. 19 with the opaque portion moved away from the central portion of the spectacle.

As shown in FIGS. 19 and 20, the spectacles 120 can have a removable opaque portion 130 that can be positioned over the central portion 132 of each lens. Preferably, the opaque portion 130 is substantially circular and is substantially the same size and shape as the central portion 132 of each lens.

As shown specifically, in FIG. 19, the opaque portion 130 blocks out or covers the central portion 132, thus eliminating or substantially eliminating light from passing through the central portion of the spectacle lenses and through the implanted lens(es) adapted to form a telescopic system. Substantially all light that enters the eye passes through the peripheral portion 134 of the spectacle lenses 120 and either focuses directly onto the peripheral portion of the retina or passes through the peripheral portion of an implanted lens and then onto a peripheral portion of the retina.

Opaque portion or member 130 is preferably connected to the frame of the spectacle by arm member 136. The arm member is preferably hinged to the spectacles in any suitable fashion. However, it is noted that the opaque portion can be coupled to any portion of the spectacles desired. For example, the opaque portion can be coupled to the lens, the central portion of the frame (i.e., at or near the nose portion), the peripheral portion of the frame or in any other suitable manner. Additionally, as described herein the opaque portion does not necessarily need to be coupled to the spectacles using a hinged arm and can be connected (or not) in any manner desired.

When the patient desires to focus at near objects (e.g., reading, driving, etc.) the opaque portion 130 can be flipped out of the way (FIG. 20) of the central portion 132 or removed in any other suitable manner. This allows light to pass through the central portion 132 of the spectacle lens(es) and pass through the telescopic portion of the lens system, thus enabling the patient to focus on a near object.

Additionally; if desired an opaque portion can be positioned to cover the peripheral portion 134 to eliminate substantially all light from entering the peripheral portion 134 of the spectacles 120. Spectacles 120 can have two concentric opaque portions: 1) the central opaque portion;

and 2) a concentric substantially ring-shaped opaque portion that can be flipped up or down, depending on the type of vision desired by the patient. For example, if the patient desired near vision, the central opaque portion can be flipped up or moved away from the central portion of the spectacles, and the substantially ring-shaped portion could be flipped down to cover the peripheral area of the spectacle lens(es). If the patient desired to see using the peripheral portion of the spectacle lens(es) the central opaque portion could be flipped down to cover the central portion and the substantially ring-shaped portion could be flipped up or moved away from the peripheral portion of the spectacle lens(es).

It is noted that each opaque portion can be used alone or in combination with any other opaque portion, and that the opaque portions can be applied or used to cover the spectacle lens(es) in any manner desired. For example, the opaque portions can be attached to the spectacles using a lever arm 136 as shown in FIGS. 19 and 20, the opaque portion can be attached using adhesive, static, the opaque portion can be applied using any type of marking device, or the opaque portions can be any device or method that would obscure a portion or all of any type of lens, spectacle, contact or any other type.

While various embodiments have been chosen to illustrate the invention, it will be understood by those skilled in the art that various changes and modifications can be made therein without departing from the scope of the invention as defined in the appended claims.

What is claimed is:

1. An intraocular lens implant kit for correcting vision in an eye, comprising:
    a first intraocular lens for replacing a natural lens, said first intraocular lens having a central portion and a peripheral portion, said central portion comprising a lens with a negative refractive index, said peripheral portion having refractive powers to correct for refractive errors in the eye; and
    a second intraocular lens adapted to be placed in said anterior chamber of said eye, said second intraocular lens having a central portion comprising a lens with a positive refractive index, wherein the first intraocular lens and the second intraocular lens are connected such that natural fluid from the eye can flow between the first intraocular lens and the second intraocular lens.

2. An intraocular lens implant kit according to claim 1, wherein said central portion of said first intraocular lens is a diffractive lens.

3. An intraocular lens implant kit according to claim 1, further comprising
    a supplemental lens adapted to be located outside the eye and cooperate with the first and second intraocular lenses.

4. An intraocular lens implant according to claim 3, wherein said supplemental lens is bifocal.

5. An intraocular lens implant kit for correcting vision in an eye having a primary lens in a posterior chamber and an anterior chamber, comprising:
    a first intraocular lens adapted to be placed on a surface of said primary lens of said eye, said lens having a peripheral portion and a central portion, said central portion having a negative refractive index, said peripheral portion having refractive powers to correct for refractive errors in the eye; and
    a second intraocular lens adapted to be placed in said anterior chamber of said eye, said second intraocular lens having a central portion with a positive refractive index, wherein the first intraocular lens and the second intraocular lens are connected such that natural fluid from the eye can flow between the first intraocular lens and the second intraocular lens.

6. An intraocular lens implant kit according to claim 5, wherein
    said primary lens is a natural lens.

7. An intraocular lens implant kit according to claim 5, wherein
    said primary lens is an artificial lens.

8. An intraocular lens implant kit according to claim 5, wherein
    said central portion of said first intraocular lens is a diffractive lens.

9. An intraocular lens implant kit according to claim 5, wherein
    said central portion of said second intraocular lens is a diffractive lens.

10. An intraocular lens implant kit according to claim 5, further comprising
    a supplemental lens adapted to be located outside the eye and cooperate with the first and second intraocular lens.

11. An intraocular lens implant kit according to claim 10, wherein said supplemental lens is bifocal.

12. An intraocular lens implant kit according to claim 10, wherein said supplemental lens includes a removable opaque portion.

13. An intraocular lens implant for correcting vision in an eye having an anterior chamber and a posterior chamber, comprising:
    a first intraocular lens portion adapted to be implanted in said posterior chamber of an eye;
    a second intraocular lens portion adapted to be implanted in said anterior chamber of an eye;
    a telescope portion connecting said first intraocular lens portion and said second intraocular lens portion, said telescope portion having a converging lens and a diverging lens aligned along an optical axis, wherein the first intraocular lens and the second intraocular lens are connected such that natural fluid from the eye can flow between the first intraocular lens and the second intraocular lens.

14. An intraocular lens according to claim 13, wherein said converging and diverging lenses are refractive lenses.

15. An intraocular lens according to claim 13, wherein said converging and diverging lenses are diffractive lenses.

16. An intraocular lens implant kit according to claim 13, further comprising
    a supplemental lens adapted to be located outside the eye.

17. An intraocular lens system for correcting vision in the eye, comprising:
    a first lens adapted to be inserted into the eye substantially along the main optical axis; and
    a second lens adapted to be inserted into the eye substantially along the main optical axis, spaced from and in series with said first lens, such that said first and second lenses form a teledioptic lens system, wherein the first lens and the second lens are positioned such that natural fluid from the eye can flow between the first lens and the second lens.

18. An intraocular lens system according to claim 17, further comprising
    a means for connecting said first and second lenses.

19. An intraocular lens system according to claim 18, wherein
    said means for connecting includes at least one strut.

20. An intraocular lens system according to claim 19, wherein
said strut is flexible.
21. An intraocular lens system according to claim 18, further comprising
a third lens substantially surrounding said second lens.
22. An intraocular lens system according to claim 21, wherein
said third lens has an opening therein and said means for connecting said first and second lenses is received in said opening.
23. An intraocular lens system according to claim 18, wherein
wherein said first lens is a minus lens and said second lens is a plus lens.
24. An intraocular lens system according to claim 23, further comprising
a third lens substantially surrounding said first lens.
25. An intraocular lens system according to claim 24, further comprising
a fourth lens substantially surrounding said second lens.
26. An intraocular lens system according to claim 17, wherein
said first lens is a minus lens and said second lens is a plus lens.
27. An intraocular lens system according to claim 26, further comprising
a third lens substantially surrounding said first lens and adapted to be inserted into the posterior chamber of the eye.
28. An intraocular lens system according to claim 27, further comprising
a fourth lens substantially surrounding said second lens and adapted to be inserted into the anterior chamber of the eye.
29. An intraocular lens system according to claim 28, wherein
said third lens has a first opening therein;
said fourth lens has a second opening therein; and
said means for connecting said first and second lenses is received in said first and second openings.
30. An intraocular lens system according to claim 28, wherein
said means for connecting said first and second lenses includes at least one flexible strut.
31. An intraocular lens system according to claim 17, further comprising
a supplemental lens adapted to be located outside the eye and cooperate with the first and second lenses.
32. An intraocular lens system according to claim 31, wherein
said supplemental lens includes a removable opaque portion.
33. An intraocular lens system according to claim 31, wherein
said removable opaque portion is coupled to the spectacle by a pivotable arm.
34. An intraocular lens system according to claim 17, wherein said first lens is coupled to said second lens by a strut.
35. An intraocular lens system according to claim 34, wherein said strut is configured such that the natural fluid of the eye can flow past said strut to flow between said first lens and said second lens.
36. A method of correcting refractive error in the eye, comprising the steps of
implanting a first lens into the eye such that said first lens is positioned substantially along the main optical axis; and
implanting a second lens in the eye such that said second lens is positioned substantially along the main optical axis and spaced from said first lens, said first and second lenses forming a teledioptic lens system, wherein the first lens and the second lens are positioned such that natural fluid from the eye can flow between the first lens and the second lens.
37. A method according to claim 36, further comprising the step of
connecting said first lens to said second lens.
38. A method according to claim 37, further comprising the steps of
inserting a first member into the posterior chamber or the eye, and
coupling the first and second lenses to the first member.
39. A method according to claim 38, further comprising the steps of
inserting a second member into the anterior chamber or the eye, and
coupling the first and second lenses to the second member.

* * * * *